United States Patent [19]

Backus et al.

[11] Patent Number: 5,674,717
[45] Date of Patent: Oct. 7, 1997

[54] RAPID METHOD FOR PREFERENTIAL COAMPLIFICATION OF TWO DIFFERENT NUCLEIC ACID SEQUENCES USING POLYMERASE CHAIN REACTION

[75] Inventors: John W. Backus, Williamson; William Harold Donish, Rochester; John Bruce Findlay, Rochester; John William H. Sutherland, Rochester; Marlene M. King, Penfield, all of N.Y.

[73] Assignee: Johnson & Johnson Clinical Diagnostics, Inc., Rochester, N.Y.

[21] Appl. No.: 548,078

[22] Filed: Oct. 25, 1995

Related U.S. Application Data

[63] Continuation of Ser. No. 371,046, Jan. 10, 1995, abandoned, which is a continuation of Ser. No. 89,987, Jul. 8, 1993, abandoned.

[51] Int. Cl.$^6$ ............................... C12P 19/34; C12Q 1/68
[52] U.S. Cl. .............................................. 435/91.2; 435/6
[58] Field of Search ........................ 435/6, 91.2, 91.33; 935/77, 78

[56] References Cited

U.S. PATENT DOCUMENTS

| | | | |
|---|---|---|---|
| 4,965,188 | 10/1990 | Mullis et al. | 435/6 |
| 5,008,182 | 4/1991 | Sninski et al. | 435/5 |
| 5,066,584 | 11/1991 | Gyllensten et al. | 435/91.2 |
| 5,079,351 | 1/1992 | Sninsky | 536/27 |
| 5,176,995 | 1/1993 | Sninsky | 435/6 |

FOREIGN PATENT DOCUMENTS 401037   1/1989   European Pat. Off. .

OTHER PUBLICATIONS

Pang et al, Nature, 343, pp. 85–89 (1990).

Kellogg et al, Anal. Biochem., 189, pp. 202–208 (Sep., 1990).

Guatelli et al, Clin. Microbiol. Rev., 2(2), pp. 217–226 (1989).

Cetvs 1990 (Biosis Abstract) WO 9003444 Apr. 5, 1990.

Kneba et al (Biosis Abstract) Leuk Lymph 3(2):109–118 (1990).

Hames et al. "Nucleic Acid Hybridization" (1987) pp. 78–83.

Able et al, Clin. Chem 36(6) 1019 (1990) "Inclusion of HCA Coamplification . . . ".

Hall et al Biotechiques 13(2):248–257 (1992) "PCR–Based Analysis of the T–Cell . . . ".

*Primary Examiner*—Eggerton A. Campbell

[57] ABSTRACT

Nucleic acids can be amplified and detected using a very rapid polymerase chain reaction procedure in which two different nucleic acid sequences are present. This method allows one to preferentially modulate (for example, suppress) the degree of amplification of one or more nucleic acid sequences relative to other nucleic acid sequences. This modulation is achieved by exploiting differences in the relative primer melt temperatures, or by using certain ratios of primers. Each PCR cycle is very fast, that is less than about 90 seconds. This method is particularly useful for amplification and detection of DNA associated with infectious agents that may be present in a specimen in very small quantities compared to other nontargeted nucleic acids.

17 Claims, No Drawings

RAPID METHOD FOR PREFERENTIAL COAMPLIFICATION OF TWO DIFFERENT NUCLEIC ACID SEQUENCES USING POLYMERASE CHAIN REACTION

This is a continuation of application Ser. No. 08/371,046, filed Jan. 10, 1995 now abandoned, which is a continuation of application Ser. No. 08/089,987, filed Jul. 8, 1993, now abandoned.

FIELD OF THE INVENTION

This invention relates to very rapid preferential amplification of two or more nucleic acid sequences, whereby a target nucleic acid sequence is readily amplified and detected while amplification of nontarget nucleic acid sequences is suppressed. The amplification technique used is polymerase chain reaction (PCR).

BACKGROUND OF THE INVENTION

Nucleic acid probe technology has developed rapidly in recent years as researchers have discovered its value for detection of various diseases, organisms or genetic features which are present in small quantities in a human or animal test sample. The use of probes is based upon the concept of complementarity. DNA has two strands bound together by hydrogen bonds between complementary nucleotides (which are also known as nucleotide pairs).

The DNA complex is normally stable, but the strands can be separated (or denatured) by conditions which disrupt the hydrogen bonding. The released single strands will reassociate only with another strand having a complementary sequence of nucleotides. This hybridization process can occur with both strands being in solution or with one of the strands being attached to a solid substrate.

A targeted nucleic acid sequence in an organism or cell may be only a very small portion of the entire DNA molecule so that it is very difficult to detect its presence using most labeled DNA probes. Much research has been carried out to find ways to detect only a few molecules of a targeted nucleic acid.

PCR is a significant advance in the art to allow detection of very small concentrations of a targeted nucleic acid. The details of PCR are described, for example, in U.S. Pat. No. 4,683,195 (Mullis et al), U.S. Pat. No. 4,683,202 (Mullis) and U.S. Pat. No. 4,965,188 (Mullis et al) and by Mullis et el, *Methods of Enzymology* 155, pp. 335–350, 1987, although there is a rapidly expanding volume of literature in this field. Without going into extensive detail, PCR involves hybridizing primers to the strands of a target nucleic acid (considered the "templates") in the presence of a polymerization agent (such as a DNA polymerase) and deoxyribonucleotide triphosphates under appropriate conditions. The result is the formation of primer extension products along the templates, the products having added thereto nucleotides which are complementary to the templates.

Once the primer extension products are denatured, one copy of the templates has been prepared, and the cycle of priming, extending and denaturation can be carried out as many times as desired to provide an exponential increase in the amount of the target nucleic acid. In effect, the target nucleic acid is duplicated (or "amplified") many times so that it is more easily detected. Despite the broad and rapid use of PCR in a variety of biological and diagnostic fields, there are still limitations which must be overcome to achieve the optimum success of the technology.

Human or animal DNA specimens contain many different nucleic acids, some of which are endogenous (or natural) to the person or animal, and others which are produced because of some abnormal condition, such as from the presence of an infectious agent (for example, virus, bacteria or parasite) or an oncogenic condition. It is these "unnatural" nucleic acids that are often desirable to detect to see if the causative organism or agent is present. Usually the nucleic acids associated with infectious agents or oncogenic conditions are present in relatively low concentration, and yet there is a desire to detect them at that concentration so as to provide early diagnosis and treatment. Such nucleic acids are often referred to as "low copy number genes" or "low copy number nucleic acids".

By comparison, the nucleic acids normally present in a human or animal being tested are often present in relatively high concentrations. Such nucleic acids are often referred to as "high copy number genes" or "high copy number nucleic acids". One such example is human β-globin DNA.

Frequently, in using PCR, two or more nucleic acids present in a specimen are amplified at the same time in the same reaction container (identified herein as "coamplification"). Coamplification requires that primers for each nucleic acid to be amplified must be simultaneously present in the container. At the end of the amplification process, all of the nucleic acids have undergone exponential growth in concentration.

Generally speaking, high copy nucleic acids will not only give high signals after PCR, but they may also lower the signals which would otherwise be obtained from amplification of the low copy nucleic acids in the same specimen. Thus, the signal from the low copy nucleic acid may be obscured or difficult to detect. False negative results would be likely, and in many instances, such as in the detection of HIV-I DNA or DNA resulting from oncogenic conditions, this would have serious consequences. In order to increase the signal of the low copy nucleic acid, skilled artisans have increased the concentrations of amplification reagent levels, but that does not always increase amplification efficiency. It also increases assay costs. In general, the high copy nucleic acid makes it more difficult to coamplify low copy nucleic acids using multiple primer sets.

Thus, there has been a serious need in the art for a way to amplify low copy nucleic acids in the presence of high copy nucleic acids in such a way that both are easy to detect and give signals of approximately equal magnitude.

One way of addressing this problem has been to vary the primer ratios so that the signal for a target low copy nucleic acid becomes comparable to that of the high copy nucleic acid. This has been referred to in the art as "primer biasing" the PCR yield, and requires a decrease in the concentration of primers for the high copy nucleic acid. The problem with this approach is that only modest control of the PCR process is achieved.

When PCR is "biased" or modulated as noted, however, by using low amounts of primers for a high copy number nucleic acid, the amplification efficiency for that nucleic acid is lowered during the entire PCR process. This can be highly undesirable since successful amplification requires that target nucleic acids (of any copy number) be duplicated in the first few PCR cycles. The failure of the nucleic acid to be replicated in those critical early cycles often leads to what is referred to as a "misfire", that is a failure to obtain amplification of that nucleic acid even though it is present in the specimen in relatively high concentrations. Thus, there is a need for greater control of PCR than can be obtained by varying the primer levels alone.

Another approach to coamplification has been to adjust the temperature of annealing in PCR such that the primers for the high copy nucleic acid anneal at a slower rate than do those for the low copy nucleic acid. This usually means annealing at a temperature slightly above the $T_m$ of the primers for the high copy nucleic acid.

This approach has a problem also. The $T_m$ difference between primer pairs must be relatively large before good modulation (or "biasing") or PCR can be exerted on the differential yields for the high and low copy nucleic acids.

Exact $T_m$'s for primers cannot be calculated (although they can be estimated), and thus they must be measured. Most workers in the art do not go to this degree of effort, and instead proceed empirically, thereby modifying the annealing temperature in PCR until they obtain the desired result. This is tedious and expensive. Thus, a need still exists for coamplification which provides greater flexibility in "biasing" the system whereby PCR proceeds vigorously, and yet the signals from amplified low and high nucleic acids can be readily adjusted.

It would be desirable to achieve high and detectable signal for a target low copy nucleic acids in the presence of a coamplified high copy nucleic acids without the problems noted above for known coamplification methods.

SUMMARY OF THE INVENTION

We have discovered an improved method for coamplification, that is a method for the amplification of two or more nucleic acids whereby the relative yields of amplified products are regulated, the method comprising the steps of:

A. heating a sample suspected of containing two or more nucleic acids, at least one of which is identified as a high copy target nucleic acid which is suspected of being present at substantially higher concentration than the low copy nucleic acids suspected of being present, at least one of which is a low copy target nucleic acid, the heating being carried out at a first temperature of from about 85° to about 100° C. for from about 1 to about 40 seconds to denature the strands of the high copy and low copy target nucleic acids, B. priming the denatured strands with a set of primers specific to and hybridizable with opposing strands of the low copy and high copy target nucleic acids to be amplified, by cooling to a second temperature, $T_2$, which is defined as:

$$(T_{mL}-15)°C. \leq T_2 \leq (T_{mL}+5)°C.$$

wherein $T_{mL}$ is the melting temperature of the primers for the low copy target nucleic acid, over a time period of from about 5 to about 20 seconds, C) forming primer extension products in the presence of
1) a thermostable DNA polymerase present in an amount of at least about 5 units/100 µl of solution, and
2) two or more deoxyribonucleotide-5'-triphosphates present in amounts effective for DNA polymerization, the products being formed by incubation for from about 1 to about 80 seconds at a third temperature, $T_3$, which is defined as:

$$(T_{mL}-15)°C. \leq T_3 \leq (T_{mL}+15)°C.,$$

the ratio of the concentration of the primed low copy target nucleic acid to the starting concentration of the unprimed low copy target nucleic acid being from about 0.95 to about 0.5, and the ratio of the concentration of the primed high copy target nucleic acid to the starting concentration of the unprimed high copy target nucleic acid being from about 0.95 to about 0.01, D) heating the primer extension products to the first temperature over a period of time of from about 5 to about 20 seconds and keeping the products at that temperature for from about 1 to about 40 seconds, and E) repeating steps B through D sequentially as a cycle at least once wherein each cycle of steps B through D is carried out from about 20 to about 90 seconds.

The present invention provides a very rapid and efficient method for preferentially amplifying and detecting a low copy nucleic acid, especially in the presence of a high copy nucleic acid which potentially could obscure the signal for the low copy target nucleic acid. Because the method is rapid, a result can be obtained in shorter time than is normally possible.

By shortening the time allowed for annealing, the benefits of varying primer ratios and adjusting primer $T_m$'s are magnified in PCR. This combination of features makes the process much more sensitive to either feature. Additional flexibility is obtained because the temperature and time conditions of PCR can be varied more readily than primer concentration or primer $T_m$ values once the method has begun. In addition, the DNA polymerase and primer concentrations are critically specified and the annealing (second) temperature is such that the priming efficiency for the high copy nucleic acid is reduced. This combination of features overcomes the problems noted above and allows for effective and rapid coamplification and detection of the low copy target nucleic acid despite the presence of high copy nucleic acids in the specimen.

DETAILED DESCRIPTION OF THE INVENTION

The general principles and conditions for amplification and detection of nucleic acids using polymerase chain reaction are quite well known, the details of which are provided in numerous references including U.S. Pat. Nos. 4,683,195, 4,683,202 and 4,965,188 (noted above), all of which are incorporated herein by reference. Thus, in view of the teaching in the art and the specific teaching provided herein, a worker skilled in the art should have no difficulty in practicing the present invention by making the adjustments taught herein to simultaneously amplify (or coamplify) two or more nucleic acids, one of which is a low copy target nucleic acid.

The present invention is directed to the amplification or detection of one or more specific nucleic acid sequences present in one or more low copy target nucleic acids in a test specimen. These nucleic acids are generally present in low concentration, or what is known in the art as "low copy" as compared to other nucleic acids in the specimen. Generally, a low copy target nucleic acid is present in a specimen in an amount of less than about $10^{-16}$ molar, however the amount can be greater if the "high copy" nucleic acids are present in much higher amounts, say at least 1000 times greater in concentration. "High copy" target nucleic acids which are also amplified by the present invention are those generally associated with genetic abnormalities, infectious agents and cancers. While such nucleic acids are amplified, the intent of the present invention is to regulate or suppress the effect of their higher concentration so the low copy target nucleic acids are more readily detectable.

In addition, the high copy target nucleic acid can be used as a "positive control" in an assay. By modulating the efficiency of PCR of the high copy target nucleic acid (which can be a ubiquitous or synthetic nucleic acid), the positive control can be made more sensitive to PCR inhibitors which may be present in the reaction system. Thus, the positive control would be detectable only if PCR was carried out efficiently, thereby reducing the probability of false positives. In such instances, the high copy target nucleic acid may be present at 10 or more times than the concentration of the low copy target nucleic acid.

Test specimens can include cellular or viral material, hair, body fluids or other materials containing genetic DNA or RNA which can be detected. While the primary purpose of detection could be diagnostic in nature, the invention could also be used to improve the efficiency of cloning DNA or messenger RNA, or for obtaining large amounts of the desired sequence from a mixture of nucleic acids resulting from chemical synthesis.

Nucleic acids to be amplified can be obtained from various sources including plasmids, and naturally occurring DNA or RNA from any source (such as bacteria, yeast, viruses, plants, higher animals or humans). It may be extracted from various tissues including blood, peripheral blood mononuclear cells (PBMC), other tissue material or other sources known in the art using known procedures. The present invention is particularly useful for the amplification and detection of nucleic acid sequences found in genomic DNA, bacterial DNA, fungal DNA, viral RNA, or DNA or RNA found in bacterial or viral infected cells. In addition, nucleic acids associated with cancers are amplifiable and detectable using the present invention.

Bacteria which can be detected include, but are not limited to, bacteria found in human blood, Salmonella species, Chlamydia species, Gonococcal species, Shigella species and Mycobacterium species. Viruses which are detectable include, but are not limited to, herpes simplex viruses, Epstein Barr virus, human cytomegalovirus, human papilloma virus, hepatitis viruses and retroviruses such as HTLV-I, HTLV-II, HIV-I and HIV-II. Protozoan parasites, yeasts and molds are also detectable. Other detectable species would be readily apparent to one skilled in the art. The invention is particularly useful for the detection of the presence of DNA associated with an infectious agent, such as a retroviral DNA and DNA associated with a Mycobacterium species. Most preferably, it is used to detect DNA associated with HIV-I.

A "PCR reagent" refers to any of the reagents considered essential to PCR, namely a set of primers for the opposing strands of each target nucleic acid, a DNA polymerase, a DNA polymerase cofactor, and two or more deoxyribonucleoside-5'-triphosphates.

The term "primer" refers to an oligonucleotide, whether naturally occurring or synthetically produced, which is capable of acting as a point of initiation of synthesis when placed under conditions in which synthesis of a primer extension product complementary to a nucleic acid strand (that is, template) is induced. Such conditions include the presence of the other PCR reagents, and suitable temperature and pH.

The primer is preferably single stranded for maximum efficiency in amplification, but may be double stranded if desired. It must be long enough to prime the synthesis of extension products in the presence of the DNA polymerase. The exact size of each primer will vary depending upon the use contemplated, the complexity of the targeted sequence, reaction temperature and the source of the primer. Generally, the primers used in this invention will have from 10 to 60 nucleotides, and preferably, they have from 18 to 45 nucleotides.

The primers in each primer set used in the present invention are selected to be "substantially complementary" to the different strands of each specific sequence to be amplified. This means that they must be sufficiently complementary to hybridize with their respective strands to form the desired hybridized products and then be extendible by a DNA polymerase. In the preferred and most practical situation, the primer has exact complementarity to the target nucleic acid.

Primers useful herein can be obtained from a number of sources or prepared using known techniques and equipment, including for example, an ABI DNA Synthesizer (available from Applied Biosystems) or a Biosearch 8600 Series or 8800 Series Synthesizer (available from Milligen-Biosearch, Inc.) and known methods for their use (for example as described in U.S. Pat. No. 4,965,188, noted above). Naturally occurring primers isolated from biological sources are also useful (such as restriction endonuclease digests). As used herein, the term "primer" also refers to a mixture of primers.

A DNA polymerase is an enzyme which will add deoxynucleoside monophosphate molecules to the 3'-hydroxy end of the primer in a complex of primer and template, but this addition is in a template dependent manner (that is, dependent upon the specific nucleotides in the template). Useful DNA polymerases include for example, E. coli DNA polymerase I, T4 DNA polymerase, Klenow polymerase, reverse transcriptase and others known in the art.

The DNA polymerase is preferably "thermostable", meaning that it is generally stable to heat and preferentially active at higher temperatures, especially the high temperatures used for denaturation of DNA strands. More particularly, the thermostable DNA polymerases are not substantially inactivated at the high temperatures used in PCR. Such temperatures will vary depending upon a number of reaction conditions, including pH, salt concentration, and other conditions known in the art.

A number of thermostable DNA polymerases have been reported in the art, including those mentioned in detail in U.S. Pat. No. 4,965,188 (noted above) and U.S. Pat. No. 4,889,818 (issued Dec. 26, 1989 to Gelfand et al). Particularly useful polymerases are those obtained from various Thermus bacterial species. Preferred thermostable enzymes are DNA polymerases obtained from *Thermus aquaticus, Thermus filiformis, Thermus flavus* or *Thermus thermophilus*. Other useful thermostable polymerases are obtained from a variety of other microbial sources including *Thermococcus literalis, Pyrococcus furiosus*, Thermotoga sp. and those described in WO-A-89/06691 (published Jul. 27, 1989). Some useful enzymes are commercially available. A number of techniques are known for isolating naturally-occurring polymerases from organisms, and cloning and other synthetic techniques for preparing polymerases using recombinant techniques, are also known from the art cited above.

A DNA polymerase cofactor refers to a nonprotein compound on which the enzyme depends for activity. A number of such materials are known in the art, including manganese and magnesium compounds which release divalent manganese or magnesium ions in the aqueous reaction mixture. Useful cofactors include, but are not limited to, manganese and magnesium salts, such as chlorides, sulfates, acetates and fatty acid salts. The smaller salts, such as chlorides, sulfates and acetates, are preferred with magnesium chlorides and sulfates being most preferred.

Also needed for PCR are two or more deoxyribonucleoside-5'-triphosphates, such as dATP, dCTP, dGTP, dTTP and dUTP. Analogues such as dITP and 7-deaza-dGTP are also useful. Preferably, the four common triphosphates (dATP, dCTP, dGTP and dTTP) are used in PCR.

Also useful in the practice of the invention is an antibody specific to the DNA polymerase, which antibody inhibits its enzymatic activity at temperatures below about 50° C., but which antibody is deactivated at higher temperatures. Representative monoclonal antibodies having these properties are described in U.S. Ser. No. 07/958,144 (filed Oct. 7, 1992 by Scalice et al). Two such monoclonal antibodies are readily obtained by a skilled artisan using conventional procedures, and starting materials including either of hybridoma cell lines HB 11126 and 11127, deposited with the American Type Culture Collection (Rockville, Md.). The monoclonal antibody is used in the practice of this invention in an amount of from about 5:1 to about 500:1 molar ratio to the DNA polymerase used (preferably from about 25:1 to about 100:1 molar ratio).

The PCR reagents described herein are provided and used in PCR in suitable concentrations to provide the differential amplification of the low copy target nucleic acid and to suppress the amplification of any high copy target nucleic acids present in the specimen.

The minimal amounts of DNA polymerase is generally at least about 5 units/100 µl of solution, with from about 10 to about 25 units/100 µl being preferred, and from about 7 to about 20 units/100 µl being more preferred. A "unit" is defined herein as the amount of enzyme activity required to incorporate 10 nmoles of total nucleotides (dNTP's) into an extending nucleic acid chain in 30 minutes at 74° C.

The concentration of primers for the low copy target nucleic acid is such that the ratio of the concentration of the primed low copy target nucleic acid to the starting concentration of the unprimed low copy target nucleic acid is from about 0.95 to about 0.5, and preferably from about 0.9 to about 0.8. The broader ratio range generally corresponds to a primer concentration of from about 0.1 to about 10 µmolar, and the narrow range corresponds to a primer concentrations of from about 0.4 to about 2 µmolar.

The concentration of primers for the high copy target nucleic acid which is also amplified is such that the ratio of the concentration of the primed high copy target nucleic acid to the starting concentration of the unprimed high copy target nucleic acid is from about 0.9 to about 0.01, and preferably from about 0.5 to about 0.25. The broader range generally corresponds to a primer concentration of from about 0.01 to about 0.8 µmolar. In a preferred embodiment, the concentration of each primer for the high copy target nucleic acid is within the range of from about 0.1 to about 0.5 µmolar.

The fraction of either the high copy or low copy target nucleic acid that is primed can be determined by synthesizing the complement of each primer, and under the given time, temperature and reagent conditions of the PCR process, measuring the amount of primed complement using UV hypochromism and conventional procedures.

The DNA polymerase cofactor is generally present in an amount of from about 2 to about 15 mmolar, and each dNTP is generally present at from about 0.25 to about 3.5 mmolar in the reaction mixture.

The PCR reagents can be supplied individually, or in a buffered solution having a pH in the range of from about 7 to about 9.

A low copy target nucleic acid can be obtained from any of a variety of sources as noted above. Generally, it must be extracted in some manner to make it available for contact with the primers and other reaction materials. This usually means removing unwanted proteins and cellular matter from the specimen in a suitable manner. Various procedures are known in the art, including those described by Laure et al in *The Lancet*, pp. 538–540 (Sep. 3, 1988), Maniatis et al, *Molecular Cloning: A Laboratory Manual*, pp. 280–281 (1982), Gross-Belland et al in *Eur. J. Biochem.*, 36, 32 (1973) and U.S. Pat. No. 4,965,188 (noted above). Extraction of DNA from whole blood or components thereof are described, for example, in EP-A-0 393 744 (published Oct. 24, 1990), Bell et al, *Proc. Natl. Acad. Sci. USA*, 78(9), pp. 5759–5763 (1981) and Saiki et al, *Bio/Technology*, 3, pp. 1008–1012 (1985).

Since the low copy target nucleic acid to be amplified and detected is usually in double stranded form, the two strands must be separated (that is, denatured) before priming can take place. This can occur during the extraction process, or be a separate step afterwards. Heating to a suitable temperature (identified as "first temperature", or $T_1$ herein) is a preferred means for denaturation. Generally, this first temperature is in the range of from about 85 to about 100° C. for a suitable time, for example from about 1 to about 40 seconds.

The denatured strands are then primed with the appropriate set of primers by cooling the reaction mixture to a second temperature, $T_2$, which is defined as $$(T_{mL}-15)°C. \leq T_2 \leq (T_{mL}+5)°C.$$

wherein $T_{mL}$ is the melting temperature of the primers for the low copy target nucleic acid. Generally, $T_2$ is within the range of from about 55 to about 70° C. Cooling takes place over a time period of from about 5 to about 20 seconds, and more preferably for from about 5 to about 15 seconds. Preferably, $T_2$ is defined as $$(T_{mL}-5)°C. \leq T_2 \leq (T_{mL}+2)°C.$$

and is in the narrower range of from about 62° to about 68° C.

Once the denatured strands are cooled to $T_2$, the reaction mixture containing the PCR reagents is incubated at a third temperature, $T_3$, for from 1 to about 80 seconds, and preferably for from 1 to about 40 seconds, to effect formation of primer extension products. Generally, $T_3$ is defined as:

$$(T_{mL}-15)°C. \leq T_3 \leq (T_{mL}+15)°C.,$$

and is in the range of from about 55 to about 70° C. Preferably, $T_3$ is defined as:

$$(T_{mL}-5)°C. \leq T_3 \leq (T_{mL}+2)°C.$$

and is in the range of from about 62° about 68° C.

In a most preferred embodiment, $T_2$ and $T_3$ are the same and are within the range of from about 62° to about 68° C.

Each primer for the high copy target nucleic acid also has a melting temperature identified herein as $T_{mH}$. The difference, $\Delta T$, between $T_{mL}$ and $T_{mH}$ is from about 2° to about 8° C., and both $T_2$ and $T_3$ are between $T_{mL}$ and $T_{mH}$ or equal to either $T_{mL}$ or $T_{mH}$.

Melting temperatures ($T_{mL}$ and $T_{mH}$) are defined herein as the temperatures at which one-half of a primer is denatured from a complementary strand (such as the template). The determination of the melting temperatures can be accomplished using several standard procedures, based on ultraviolet hypochromism, for example, by monitoring the spectrum at 260 nm as described in *Biochemistry—The Molecular Basis of Cell Structure and Function*, 2nd Edition, Lehninger, Worth Publishers, Inc., 1970, pp. 876–7. The various methods of determining melting temperatures may produce slightly differing values for the same DNA molecule, but those values should not vary from each other by more than about 2° or 3° C.

Preferably, the melting temperatures are calculated using the formula:

$$T_m(°C.)=67.5+0.34(\% \ G+C)-395/N$$

wherein "G" and "C" represent the number of guanine and cytosine nucleotides, respectively, and "N" represents the total number of nucleotides in the oligonucleotide (that is, primer). Melting temperature values obtained by this calculation correlate very well with the values determined empirically at room temperature using conventional UV hypochromism and a conventional Hewlett-Packard diode array spectrophotometer (scanning rate of about +1° C./min.) for a solution of primer in 10 mmolar tris(hydroxymethyl) aminomethane buffer (pH 8.5) having an ionic strength of at least about 60 mmolar provided by one or more inorganic or organic salts, such as magnesium chloride, magnesium sulfate, potassium chloride, sodium chloride and others readily apparent to one skilled in the art. The amounts of primer and its complement in the solution used to determine the noted melting temperature formula were sufficient to provide an optical density of from about 0.5 to about 1.0 OD units.

After formation of primer extension products, the reaction mixture is heated to $T_1$ over a period of time of from about 5 to about 20 seconds, and maintained at that temperature for from about 1 to about 40 seconds. This completes an amplification cycle.

PCR is generally carried out for at least 20 cycles, with 20 to 50 cycles being preferred. Each cycle is generally from about 20 to about 90 seconds, with a cycle time of from about 30 to about 75 seconds being preferred.

The amplification method of this invention is preferably conducted in a continuous, automated manner so that the reaction mixture is temperature cycled in a controlled manner for a desired number of times. A number of instruments have been developed for this purpose, as one of ordinary skill in the art would know.

One such instrument for this purpose is described in some detail in U.S. Pat. No. 4,965,188 and EP-A-0 236,069. Generally, this instrument includes a heat conducting container for holding a number of reaction tubes containing reaction mixture, a means for heating, cooling and temperature maintenance, and a computing means to generate signals to control the amplification sequence, changes in temperature and timing.

A preferred instrument for processing amplification reactions in a disposable chemical test pack is described in some detail in U.S. Pat. No. 5,089,233 (Devaney, Jr. et al), incorporated by reference. In general, this instrument comprises a surface for supporting chemical test packs, pressure applicators supported above the surface for acting on the reaction pack to transfer fluids between adjacent chambers in the test pack, and means for operating the pressure applicators through a range of movement extending across the test pack.

EP-A-0 402 994 provides details of useful chemical test packs which can be processed using the instrument described in U.S. Pat. No. 5,089,233 (noted above). Also described therein are means for heating and cooling the test pack at repeated intervals (that is, through cycles) appropriate for the method of the present invention. Further details regarding useful PCR processing equipment can be obtained from the considerable literature in the field, and would be readily ascertainable by one skilled in the art.

Besides chemical test packs described above, the method can be carried out in other containers such as those described in more detail in U.S. Pat. No. 4,902,624 (Columbus et al), U.S. Pat. No. 5,173,260 (Zander et al) and recently allowed U.S. Ser. No. 07/962,159 (filed Oct. 15, 1992 by Schnipelsky et al), all incorporated herein by reference. Such test packs have a multiplicity of reaction chambers containing various reagents, buffers and other materials which are useful at various stages in the amplification or detection method.

After the desired number of cycles, the reaction can be stopped by inactivating the DNA polymerase using known techniques, or by separating the components of the reaction.

As noted above, the method of this invention can be used to detect or characterize a low copy target nucleic acid. Detection can be accomplished in a number of known ways, such as those described in U.S. Pat. No. 4,965,188 (noted above). For example, the amplified nucleic acid can be analyzed using Southern blotting techniques. Alternatively, amplification can be carried out using radioisotopic or biotinylated primers which can then be detected using appropriate techniques.

In one embodiment, once a desired amount of the nucleic acid sequence of interest has been generated and the primer extension products are denatured for a last time, the amplified target nucleic acid is detected using an oligonucleotide probe which is labeled for detection and is complementary to one of the primer extension products. Procedures for attaching labels and preparing probes are well known in the art, for example, as described by Agrawal et al, *Nucleic Acid Res.*, 14, pp. 6227–45 (1986), U.S. Pat. No. 4,914,210 (Levenson et al) relating to biotin labels, U.S. Pat. No. 4,962,029 (Levenson et al) relating to enzyme labels, and the references noted therein. Useful labels include radioisotopes, electron-dense reagents, chromogens, fluorogens, phosphorescent moieties, ferritin and other magnetic particles (see U.S. Pat. No. 4,795,698 of Owen et al and U.S. Pat. No. 4,920,061 of Poynton et al), chemiluminescent moieties and enzymes (which are preferred). Useful enzymes include, glucose oxidase, peroxidase, uricase, alkaline phosphatase and others known in the art. Substrates and dye forming compositions for such enzymes are well known.

Where the label is a preferred enzyme such as peroxidase, at some point in the assay, hydrogen peroxide and suitable dye-forming compositions are added to provide a detectable dye. For example, useful dye-providing reagents include tetramethylbenzidine and derivatives thereof, and leuco dyes, such as triarylimidazole leuco dyes (as described in U.S. Pat. No. 4,089,747 of Bruschi), or other compounds which react to provide a dye in the presence of peroxidase and hydrogen peroxide. Particularly useful dye-providing compositions are described in U.S. Pat. No. 5,024,935 (McClune et al). Chemiluminescent signals can be generated using acridinium salts or luminol and similar compounds in combination with enhancers in the presence of peroxidase.

Detection of the presence of the probe which is in the complementary product can be achieved using suitable detection equipment and procedures which are well known.

In a preferred embodiment, one or both of the primers in each primer set used to detect a target nucleic acid is labeled with a specific binding moiety. The specific binding moiety can be the same or different for each set of primers. Such labels include any molecule for which there is a receptor molecule that reacts specifically with the specific binding moiety. Examples of specific binding pairs (one of which can be the label) include, but are not limited to, avidin/biotin, streptavidin/biotin, sugar/lectin, antibody/hapten, antibody/antigen and others readily apparent to one skilled in the art. The receptor is then conjugated with a detectable label moiety, such as an enzyme using known technology.

Most preferably, one or both primers of each primer set are labeled with biotin (or an equivalent derivative thereof), and the amplified low copy target nucleic acid is detected using a conjugate of avidin (or streptavidin) with an enzyme. The enzyme attached to the specific binding complex is then detected using the appropriate substrate reagents.

In order for the amplified target nucleic acid to be detected, it is often useful (but not necessary) for it to be separated from the other materials in the reaction medium. This is done by any of a number of ways, including using a capture reagent having a capture probe which is covalently attached to a water-insoluble support. The capture probe hybridizes with the amplified target nucleic acid and the captured material can then be separated from unhybridized materials in a suitable manner, such as by filtration, centrifugation, washing or other suitable separation techniques.

Capture probes can be attached to water-insoluble supports using known attachment techniques. One such technique is described in EP-A-0 439 222 (published Sep. 18, 1991). Other techniques are described for example in U.S. Pat. No. 4,713,326 (Dattagupta et al), U.S. Pat. No. 4,914,210 (Levenson et al) and EP-B-0 070 687 (published Jan. 26, 1983). Useful separation means are microporous filtration membranes such as the polyamide membranes marketed by Pall Corp. (for example as LOPRODYNE™ or BIODYNE™ membranes) which can be used to separate captured target nucleic acids from unhybridized materials.

Any useful solid support can be used for separation of water-insoluble product for detection, including a microtiter plate, test tube, beaker, beads, film, membrane filters, filter papers, gels, magnetic particles or glass wool. It can be made of a number of materials including glass, ceramics, metals, naturally occurring or synthetic polymers, cellulosic materials, filter materials and others readily apparent to one of ordinary skill in the art. Particularly useful solid support materials are polymeric or magnetic particles generally having an average particle size of from about 0.001 to about 10 μmeters. Further details about such preferred polymeric particles, including useful monomers, methods of preparing them and attachment of receptor molecules, are provided in U.S. Pat. No. 4,997,772 (Sutton et al), U.S. Pat. No. 5,147, 777 (Sutton et al), U.S. Pat. No. 5,155,166 (Danielson et al), all of which are incorporated herein by reference.

The detection can also be carried out by immobilizing a capture probe or capture reagent on a flat substrate, such as the microporous filtration membranes described above, or on thin polymeric films, uncoated papers or polymer coated papers, a number of which are known in the art. Other details about such materials are provided in U.S. Ser. No. 07/571, 560 (filed Sep. 4, 1990 as a CIP of U.S. Ser. No. 07/306,954, filed Feb. 3, 1989 by Findlay et al, and corresponding to EP-A-0 408 738, published Jan. 23, 1991).

Particularly useful arrangements of a capture reagent are described, for example, in U.S. Ser. No. 07/837,772 (filed Feb. 18, 1992 by Sutton et al, corresponding to WO 92/16659, published Oct. 1, 1992) and U.S. Pat. No. 5,173, 260 (Sutton et al). The capture probes are covalently attached (either directly or through chemical linking groups) to the same type of polymeric particles, and the resulting capture reagents are immobilized on a heat or ultrasonic sealable support (for example, a sheet, membrane, fibrous mat, film). One particularly useful sealable support is a laminate of polyethylene,and a polyester such as polyethylene terephthalate. The capture reagents can be disposed in distinct regions on the water-insoluble support which is part of a suitable test device (as described above). Such test devices can also be defined as diagnostic elements. For example, the support can have disposed thereon a plurality of stripes or spots of various capture reagents.

The following examples are included to illustrate the practice of this invention, and are not meant to be limiting in any way. All percentages are by weight unless otherwise noted.

Materials and Methods for Examples:

Recombinant DNA polymerase from *Thermus aquaticus* was prepared using known procedures, such as that described in EP-A-0 482 714 (noted above) and had an activity of about 250,000 units/mg of protein. The DNA polymerase was used in an amount of about 7.5–8 units/100 μl of reaction mixture.

The primers and probes were prepared using known starting materials and procedures using an Applied Biosystems Model 380B, three column DNA synthesizer using standard phosphoramidite chemistry and the ABI 1 μmolar scale, fast cycle protocol. Nucleoside-3'-phosphoramidites and nucleoside derivatized controlled pore glass supports were obtained from Applied Biosystems. The primers had the sequences identified below. They were functionalized at the 5' end with two tetraethylene glycol spacers followed by a single commercially available DuPont biotin phosphoramidite. The probes were functionalized at the 3' end with two tetraethylene glycol spacers followed by a single aminodiol linking group according to U.S. Pat. No. 4,914,210 (noted above). All purifications were carried out using a nucleic acid purification column, followed by reversed phase HPLC techniques.

Deoxyribonucleotides (dNTP's) were obtained from Sigma Chemical Co.

The "TP4" monoclonal antibody specific to the noted DNA polymerase was prepared as described in U.S. Ser. No. 07/958,144 (filed Oct. 7, 1992 by Scalice et al). Generally, it was prepared from the immune cells of DNA polymerase immunized mice using conventional procedures, such as those described by Milstein et al, *Nature* 256, pp. 495–497, 1975 and hybridoma cell lines (either HB 11126 or 11127 from ATCC), whereby antibody secreting cells of the host animal were isolated from lymphoid tissue (such as the spleen) and fused with SP2/0-Ag14 murine myeloma cells in the presence of polyethylene glycol, diluted into selective media and plated in multiwell tissue culture dishes. About 7–14 days later, the hybridoma cells containing the antibodies were harvested, and purified using conventional techniques.

The polymerase chain reaction (PCR) mixture (100 ml) included tris(hydroxymethyl)aminomethane buffer (10 mmolar, pH 8), potassium chloride (50 molar), magnesium chloride (10 mmolar), dATP, dCTP, dGTP and dTTP (1.5 molar of each), primers (identified below, 1 μmolar of each, unless otherwise indicated), gelatin (0.01%), the noted thermostable DNA polymerase (7.5–8 units/100 ml), and the TP4 monoclonal antibody (50:1 molar ratio to DNA polymerase).

The primers used in Example 1 for the amplification and detection of HIV-I DNA (aaa region) had the following sequences:

SEQ ID NO:1: 5'-X-TTTGGTCCTT GTCTTATGTC CAGAATGC-3' and

SEQ ID NO:2: 5'-X-ATAATCCACC TATCCCAGTA GGAGAAAT-3' wherein X represents biotin attached to the oligonucleotide through two aminotetraethylene glycol spacer groups using the procedures described in U.S. Pat. No. 4,962,029 (noted above).

The primers for the amplification and detection of HIV-I DNA (gag region) used in Example 2 were as follows:

SEQ ID NO:3: 5'-X-CTAAAGGGTT CCTTTGGTCC TTGTCTTATG TCCAGAATGC-3' and SEQ ID NO:4: 5'-X-GATGGATGAC AAATAATCCA CCTATCCCAG TAGGAGAAAT-3' wherein X is as defined above.

The primers for the amplification and detection of β-globin DNA in both examples were as follows:

SEQ ID NO:5: 5'-X-CAACTTCATC CACGTTCACC-3' and

SEQ ID NO:6: 5'-ACACAACTGT GTTCACTAGC-3' wherein X is as defined above.

An strept avidin-peroxidase conjugate solution comprised a commercially available (Zymed Laboratories, Inc.) conjugate of strept avidin and horseradish peroxidase (126 µl/l), casein (0.5%) and merthiolate (0.5%) in phosphate buffered saline solution (25 mmolar sodium phosphate and 75 mmolar sodium chloride). The final conjugate concentration was 312 ng/ml.

A wash solution (pH 7.4) contained sodium phosphate, monobasic 1-hydrate (25 mmolar), sodium chloride (373 mmolar), (ethylenedinitrilo)tetraacetic acid disodium salt (2.5 mmolar), ethylmercurithiosalicylic acid sodium salt (25 µmolar), and decyl sodium sulfate (38 mmolar).

The dye-providing composition (pH 6.8) contained 4,5-bis(4-dimethylaminophenyl)-2-(4-hydroxy-3-methoxyphenyl)imidazole (250 µmolar), poly(vinyl pyrrolidone) (112 mmolar), diethylenetriaminepentaacetic acid (100 µmolar), 4'-hydroxyacetanilide (5 mmolar) and sodium phosphate, monobasic, 1-hydrate (10 mmolar).

HIV-I low copy target nucleic acid was extracted from the 8E5/LAV cell line (a cell line which contains a single integrated copy of the HIV-I genome) using conventional procedures, and following cell lysis and protein digestion, was purified by phenol/chloroform extraction: tris-saturated phenol (750 µl) was added to the cell suspension, and phenol/lysate solutions were mixed and separated by centrifugation. The aqueous phase was then transferred into a fresh 2 ml tube. This procedure was repeated using chloroform isoamyl alcohol. The aqueous layer was brought to 0.3 molar sodium acetate. Nucleic acids were precipitated by adding 95% cold ethanol and storing at −70° C. for 1 hour. The concentration of HIV-I DNA was then determined at $A_{260}$ and serial dilutions of varying copy number were made in TE buffer [tris(hydroxymethyl)aminomethane (1 mmolar) and (ethylenedinitrilo)tetraacetic acid (0.1 mmolar)] for experimental use. A sample (5–10 µl) of each diluted solution was added to each PCR reaction mixture (200 µl).

The β-globin high copy target nucleic acid was obtained in human placental DNA (0.5 mg/ml) which is assumed to have two copies of the β-globin gene per cell.

The captobin probe for HIV-I DNA was as follows:

SEQ ID NO:7: 5'-ATCCTGGAAT TAAATAAAAT AGTAAGAATG TATAGCCCTA C-Y-3' wherein Y comprises two tetraethylene glycol spacers followed by a single aminediol linking group.

The capture probe for β-globin DNA was as follows:

SEQ ID NO:8: 5'-CCTCAAACAG ACACCATGGT GCACCTGACT C-Y-3' wherein Y is as defined above.

Capture reagents were prepared by attaching the capture probes identified above to particles of poly[styrene-co-3-(p-vinylbenzylthio)propionic acid] (95:5 molar ratio, 1 µm average diameter) in the following manner. A suspension of the particles in water was washed twice with 2-(N-morpholino)ethanesulfonic acid buffer (0.1 molar, pH 6), and suspended to approximately 10% solids. A sample (3.3 ml) of the washed particles, diluted to 3.33% solids in the buffer (0.1 molar), was mixed with 1-(3-dimethylaminopropyl)-3-ethylcarbodiimide hydrochloride (2.1 ml of 84 mg/ml water) and the appropriate probe (983 µl of 44.44 OD/ml nanopure water). The resulting suspension was heated at 50° C. in a water bath for about two hours with intermittent mixing and centrifuged. The particles were washed three times with tris(hydroxymethyl)aminomethane buffer (0.01 molar, pH 8) containing (ethylenedinitrilo)tetraacetic acid disodium salt (0.0001 molar) and resuspended therein to 4% solids. Upon dilution to 0.25% solids, the capture reagents were applied (1.2 µl) and dried in defined regions of the microporous membranes (LOPRODYNE™ polyamide membrane, 5 µm average pore size, from Pall Corp.) in the test wells of SURECELL™ disposable test devices (commercially available from Eastman Kodak Company), which are described, for example, in U.S. Pat. No. 4,948,561 (Hinckley et al).

PCR was carried out in disposable chemical test packs which contained chambers for individual reagents and solutions. These chambers were formed from a sheet of polyester (0.01 cm thickness) coated with polyethylene (SCOTCH PAK™ from 3M Co.), folded over to provide a circular chamber about 1.3 cm in diameter. An opening was provided to permit the addition of the PCR reagent mixture which was drawn into the chamber by vacuum. The opening was then heat sealed. After amplification, a corner of the chamber was cut, and the reaction mixture was transferred to a microfuge tube (0.5 ml) for storage at 4° C. until detection of the products was carried out. The PCR protocol was carried out using an automated Kodak PCR processor which is described in detail in U.S. Pat. No. 5,089,233, which is incorporated herein by reference, using cycles of the heating and cooling protocol described below.

The PCR reaction mixture contained 25 copies of the HIV-I low copy target nucleic acid and about 1 million copies of the β-globin high copy target nucleic acid.

Detection of the amplification products using the SURECELL™ test devices was carried out by mixing a portion (5 µl) of the amplification product reaction mixture with a buffer solution (10 mmolar, sodium dihydrogen phosphate, 150 mmolar sodium chloride and 1 mmolar ethylenediaminetetraacetic acid, pH 7.4) (95 µl) and incubated at 95° C. for 5 minutes to denature the nucleic acids. The resulting solution was then transferred to the SURECELL™ test devices to hybridize the amplified target nucleic acids to the immobilized capture reagents on the membranes at 50° C. The test wells of the test devices were washed with a solution (250 µl) of sodium decyl sulfate (1%) in the buffer solution noted above at 55° C. The strept avidin-peroxidase conjugate solution (50 µl) was added to each test well and allowed to flow through the membranes at room temperature. After two minutes, the test wells were washed again. The dye-providing composition (100 µl) was added, and the devices were incubated at room temperature for two minutes. A solution (100 μl) of sodium azide (0.1%) was added to stop dye development, and the resulting dye signal was visually graded on a density scale of 0 to 10 (highest density). Background readings were obtained from the regions on the membranes where no capture reagent had been deposited.

For Example 2, gel electrophoresis was carried out by adding the amplification product mixture (6.75 μl) to agarose gels (4%) which had been prestained with ethidiumbromide (4 μl, 10 mg/ml). The gels were electrophoresed at about 160 volts/cm for about 1 hour using an electrophoresis buffer (600 ml) containing ethidiumbromide (24 μl). The buffer was a mixture of tris(hydroxymethyl)aminomethane, borate and ethylenediaminetetraacetic acid. The resulting bands were compared to molecular weight markers, and the product band intensity was scored (129-mer for HIV-I DNA and 110-mer for β-globin DNA) on a 0 to 5 scale with 0 representing no detectable signal, and 5 representing the highest signal.

The PCR protocol carried out in the test packs was as follows:

(A) initial denaturation of nucleic acids at 95° C. for 3 minutes, and (B) 40 cycles of:
  (1) cooling to 64°–68° C. over 10–12 seconds,
  (2) forming primer extension products at 64° to 68° C., as indicated for noted times,
  (3) heating to 95° C. over an average period of 6–7 seconds, and
  (4) denaturation at 95° C. for 3 seconds.

Other reagents and materials were obtained either from commercial sources or prepared using readily available starting materials and conventional procedures.

EXAMPLE 1

Method for Coamplification of HIV-I DNA and DNA of β-Globin DNA Using Different Primer Levels This example demonstrates the practice of this invention to detect a low copy target nucleic acid (HIV-I DNA) when a high copy target nucleic acid (β-globin DNA) is present by manipulating the primer concentrations for both target nucleic acids. Moreover, the length of time used for formation of primer extension products at 65° C. was varied so the effect of primer concentration could be observed. As the results shown in Table I below demonstrate, the use of faster PCR cycles (that is, short times for primer extension) enables one to reduce amplification efficiency for the high copy target nucleic acid, and thereby to reduce its signal so the signal from the amplified low copy target nucleic acid is more readily seen.

Both HIV-I DNA and β-globin DNA were amplified using the primers described above (1 μmolar of each). It can be seen from the results that the level of inhibition of amplification of the high copy target nucleic acid was increased as the time for primer extension was decreased. Moreover, as the concentration of β-globin DNA primers was decreased to 2.5 or more times lower than the concentration of the HIV-I DNA primers, HIV-I DNA amplification proceeded more efficiently. At all times for primer extension, a concentration of β-globin primer was observed below which the high copy target nucleic acid was not amplified efficiently. Amplification of the high copy target nucleic acid was more sensitive to primer concentration when the primer extension times were shortest (that is, less than about 80 seconds).

TABLE I

| Primer Extension Time | β-globin DNA Primer Concentration (μmolar) | Dye-Signals HIV-I DNA | Dye-Signals β-globin DNA |
|---|---|---|---|
| 10 sec | 1 | 1.25 | 9.5 |
| " | 0.4 | 4.75 | 4.0 |
| " | 0.2 | 4.75 | 0.0 |
| " | 0.1 | 4.5 | 0.0 |
| " | 0.05 | 4.5 | 0.0 |
| " | 0.025 | 4.5 | 0.0 |
| 20 sec | 1 | 1.75 | 9.5 |
| " | 0.4 | 8.5 | 9.5 |
| " | 0.2 | 8.75 | 3.5 |
| " | 0.1 | 9.25 | 0.0 |
| " | 0.05 | 9.25 | 0.0 |
| " | 0.025 | 9.5 | 0.0 |
| 40 Sec | 1 | 3.5 | 9.5 |
| " | 0.4 | 8.5 | 9.25 |
| " | 0.2 | 9.0 | 9.25 |
| " | 0.1 | 8.75 | 5.25 |
| " | 0.05 | 9.0 | 0.0 |
| " | 0.025 | 9.0 | 0.0 |
| 80 sec | 1 | 8.0 | 9.75 |
| " | 0.4 | 8.5 | 9.5 |
| " | 0.2 | 8.75 | 9.5 |
| " | 0.1 | 9.0 | 6.25 |
| " | 0.05 | 9.0 | 3.25 |
| " | 0.025 | 9.0 | 0.0 |
| 160 sec | 1 | 9.5 | 10.0 |
| " | 0.4 | 9.25 | 10.0 |
| " | 0.2 | 9.25 | 10.0 |
| " | 0.1 | 9.25 | 9.25 |
| " | 0.05 | 9.25 | 8.75 |
| " | 0.025 | 9.0 | 3.0 |

EXAMPLE 2

Coamplification Using Different Melting Temperatures of Primers

This example demonstrates the practice of this invention to modulate (that is, decrease) the efficiency of PCR for the high copy target nucleic acid using primers having different $T_m$ values. PCR efficiency is therefore decreased by carrying out primer extension at a temperature higher than the $T_m$ of the primers for the high copy target nucleic acid. Under the conditions of this invention, that is rapid PCR cycles (e.g. 20 second primer extension), the effect of the modulation of PCR efficiency is increased.

In this example, HIV-I DNA was present at 25 copies and β-globin DNA was present at about $10_6$ copies. The primers (SEQ ID NO:5 and SEQ ID NO:6) for β-globin DNA had $T_m$ values of 64.5° and 67° C., respectively. The HIV-I DNA primers (SEQ ID NO:3 and SEQ ID NO:4) had $T_m$ values of 72° and 74° C., respectively. Each primer was present in the PCR reaction mixture at 1 μmolar and 7.5 units/100 μl of DNA polymerase were used. PCR was carried out as described in the protocol noted above.

The results are shown below in Table II. As the results indicate, both target nucleic acids were amplified at the lower primer extension temperatures (64°–66° C.) in separate reactions, as indicated by the dye density signals and gel electrophoresis. However, at those temperatures, the signal from the high copy target nucleic acid was too strong under both "rapid" (i.e. 20 seconds for primer extension) and "slow" (i.e. 120 seconds for primer extension) cycling conditions.

As the primer extension temperature was increased to 67° and 68° C., the signal from the high copy target nucleic acid decreased slightly under the "slow" cycling conditions. Under the "rapid" cycling conditions, the signal from the high copy target nucleic acid was decreased significantly. At 68° C., there was no detectable gel band for the β-globin DNA.

When the two target nucleic acids were amplified in the same reaction mixture (that is, coamplified) using "slow" cycling conditions, amplification appeared to be efficient for both over the entire temperature range, and neither nucleic acid appeared to have a significant effect on the other. As the primer extension temperature was increased, the signal for HIV-I DNA (gel band intensity) increased slightly while the signal for β-globin DNA decreased. At 68° C., the two signals were generally equivalent.

When the two nucleic acids were amplified at 64° C. under "rapid" cycling conditions, amplification efficiency of HIV-I DNA was reduced considerably such that there was no detectable HIV-I DNA dye or electrophoretic signal. As the primer extension temperature was increased to 67° C., there was a steady increase in the signal for HIV-I DNA and a reduction of the β-globin DNA signal so that the signals were substantially equivalent. When 68° C. was used as the primer extension temperature, the signal for β-globin DNA was completely absent so that the signal for HIV-I DNA was readily apparent.

TABLE II

| Denaturation/ Primer Extension Temperatures | Primer Extension Time | Primers Present | | Gel Band Intensity | | Dye Signals | |
|---|---|---|---|---|---|---|---|
| | | HIV-I | β-globin | HIV-I | β-globin | HIV-I | β-globin |
| 95° C./64° C. | 20 sec | + | | 1.0 | 0.0 | 7.75 | 0.0 |
| " | " | | + | 0.0 | 4.0 | 0.0 | 9.75 |
| " | " | + | + | 0.0 | 4.0 | 0.0 | 9.75 |
| 95° C./64° C. | 120 sec | + | | 1.5 | 0.0 | 8.5 | 0.0 |
| " | " | | + | 0.0 | 5.0 | 0.0 | 9.25 |
| " | " | + | + | 1.5 | 5.0 | 7.75 | 9.25 |
| 95° C./65° C. | 20 sec | + | | 0.75 | 0.0 | 7.5 | 0.0 |
| " | " | | + | 0.0 | 3.5 | 0.0 | 9.75 |
| " | " | + | + | 0.0 | 3.5 | 1.25 | 9.75 |
| 95° C./65° C. | 120 sec | + | | 1.125 | 0.0 | 8.25 | 0.0 |
| " | " | | + | 0.0 | 4.5 | 0.0 | 10 |
| " | " | + | + | 1.25 | 4.5 | 8.5 | 10 |
| 95° C./66° C. | 20 sec | + | | 0.5 | 0.0 | 7.25 | 0.0 |
| " | " | | + | 0.0 | 3.5 | 0.0 | 9.75 |
| " | " | + | + | 0.25 | 3.0 | 6.75 | 9.75 |
| 95° C./66° C. | 120 sec | + | | 1.75 | 0.0 | 8.5 | 0.0 |
| " | " | | + | 0.0 | 4.5 | 0.0 | 10 |
| " | " | + | + | 1.625 | 4.5 | 7.75 | 9.75 |
| 95° C./67° C. | 20 sec | + | | 0.75 | 0.0 | 8.0 | 0.0 |
| " | " | | + | 0.0 | 0.875 | 0.0 | 8.25 |
| " | " | + | + | 0.25 | 0.75 | 8.5 | 7.25 |
| 95° C./67° C. | 120 sec | + | | 2.0 | 0.0 | 9.0 | 0.0 |
| " | " | | + | 0.0 | 4.0 | 0.0 | 9.75 |
| " | " | + | + | 2.0 | 4.0 | 8.75 | 9.5 |
| 95° C./68° C. | 20 sec | + | | 2.0 | 0.0 | 9.25 | 0.0 |
| " | " | | + | 0.0 | 0.0 | 0.0 | 1.25 |
| " | " | + | + | 2.0 | 0.0 | 8.5 | 0.0 |
| 95° C./68° C. | 120 sec | + | | 3.0 | 0.0 | 8.5 | 0.0 |
| " | " | | + | 0.0 | 3.5 | 0.0 | 9.25 |
| " | " | + | + | 2.5 | 3.0 | 8.0 | 9.5 |

The invention has been described in detail with particular reference to preferred embodiments thereof, but it will be understood that variations and modifications can be effected within the spirit and scope of the invention.

We claim:

1. A method for the amplification of two or more target nucleic acids whereby the relative yields of amplified products are regulated, said method comprising the steps of:
  A) heating a sample suspected of containing two or more target nucleic acids, at least one of which is identified as a high copy target nucleic acid which is suspected of being presented at at least 1000 times higher concentration than the low copy nucleic acids suspected of being present, at least one of which is a low copy target nucleic acid,
    the heating being carried out at a first temperature, $T_1$, of from 85° to 100° C. for from 1 to 40 seconds to denature the strands of said high copy target and low copy target nucleic acids,
  B) priming said denatured strands with a set of primers specific to and hybridizable with opposing strands of each target nucleic acid to be amplified, by cooling to a second temperature, $T_2$, which is defined as:

$$(T_{mL}-15)°C. \leq T_2 \leq (T_{mL}+5)°C$$

wherein $T_{mL}$ is the melting temperature of the primers for the low copy target nucleic acid, over a time period of from 5 to 20 seconds,
  C) forming primer extension products in the presence of
    1) a thermostable DNA polymerase present in an amount of at least 5 units/100 µl of solution, and
    2) four or more deoxyribonucleotide-5' triphosphates present in amounts effective for DNA polymerization, said products being formed by incubation for from 1 to 40 seconds at $T_2$,
    the ratio of the concentration of the primed low copy target nucleic acid to the starting concentration of the unprimed low copy target nucleic acid being from 0.95 to 0.5, and
    the ratio of the concentration of the primed high copy target nucleic acid to the starting concentration of the unprimed high copy target nucleic acid being from 0.9 to 0.01,
  D) heating said primer extension products to said first temperature, $T_1$, over a period of time of from 5 to 20 seconds and keeping said products at said temperature for from 1 to 40 seconds, and
  E) repeating steps B through D sequentially as a cycle at least once wherein each cycle of steps B through D is carried out from 20 to 90 seconds.

2. The method of claim 1 wherein the concentration of each primer for the high copy target nucleic acid is within the range of from 0.01 to 0.8 µmolar and the concentration of each primer for the low copy target nucleic acid is within the range of from 0.1 to 10 µmolar.

3. The method of claim 1 wherein the difference, $\Delta T$, between the $T_{mL}$ and $T_{mH}$ is from 2 to 6° C., wherein $T_{mH}$ is the melting temperature for the high copy target nucleic acid, and $T_2$ is between $T_{mL}$ and $T_{mH}$ or equal to either $T_{mL}$ or $T_{mH}$.

4. The method of claim 1 wherein said target low copy nucleic acid is associated with an infectious agent.

5. The method of claim 4 wherein said target low copy nucleic acid is associated with a viral infectious agent.

6. The method of claim 1 $T_2$ is defined as:

$(T_{mL}-5)°C. \leq T_2 \leq (T_{mL}+2)°C.$

7. The method of claim 1 wherein the concentration of the primed low copy target nucleic acid to the starting concentration of the unprimed low copy target nucleic acid is from 0.9 to 0.8, and
  the ratio of the concentration of the primed high copy target nucleic acid to the starting concentration of the unprimed high copy target nucleic acid is from 0.5 to 0.25.

8. The method of claim 1 wherein one or both of the primers specific for the target low copy nucleic acid are biotinylated, and detection of said target low copy nucleic acid is carried out by capturing the resulting amplified biotinylated strand using an insolubilized oligonucleotide complementary thereto, and detecting said biotinylated strand with detectably labeled avidin.

9. The method of claim 1 wherein $T_2$ is from 55° to 70° C., step B is carried out for a time of from 5 to 15 seconds, and step C is carried out for from 1 to 40 seconds.

10. The method of claim 1 carried out using a set of primers specific for human immunodeficiency virus-I DNA which is the target low copy nucleic acid, and a set of primers specific for β-globin DNA which is the high copy nucleic acid.

11. The method of claim 1 wherein said high copy target nucleic acid is a positive control.

12. The method of claim 1 wherein said thermostable DNA polymerase is present at a concentration of from 7 to 20 units/100 µl of solution, and the concentration of each primer specific for said low copy target nucleic acid is from 0.1 to 2 µmolar.

13. The method of claim 1 wherein each cycle of Steps B through D is carried out within 30 to 75 seconds.

14. The method of claim 1 further comprising the step:

F) detecting the amplified low copy target nucleic acid after the last cycle of steps B) through D) by hybridizing said amplified low copy target nucleic acid with a capture probe.

15. The method of claim 14 wherein said capture probe comprises an oligonucleotide which is specific to and hybridizable with one of the amplified strands of said low copy target nucleic acid, said oligonucleotide being covalently attached to a magnetic or polymeric particle.

16. The method of claim 15 wherein said amplified low copy target nucleic acid is contacted with a labeled species which is reactive therewith, and detection of the signal produced from reacted or unreacted labeled species.

17. The method of claim 16 wherein said reactive labeled species is a conjugate of strept avidin with an enzyme.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
( A ) LENGTH: 28 nucleotides
( B ) TYPE: Nucleic acid
( C ) STRANDEDNESS: Single
( D ) TOPOLOGY: Linear (ii) MOLECULE TYPE: Primer for HIV-I DNA (iii) HYPOTHETICAL: No (iv) ANTI-SENSE: No (vi) ORIGINAL SOURCE: Synthetically prepared (vii) IMMEDIATE SOURCE: Same (x) PUBLICATION INFORMATION: US-A-5,147,777

(xi) SEQUENCE DESCRIPTION: SEQ ID NO:1:
TTTGGTCCTT GTCTTATGTC CAGAATGC    28

(2) INFORMATION FOR SEQ ID NO:2:

(i) SEQUENCE CHARACTERISTICS:
(A) LENGTH: 28 nucleotides
(B) TYPE: Nucleic acid
(C) STRANDEDNESS: Single
(D) TOPOLOGY: Linear (ii) MOLECULE TYPE: Primer for HIV-I DNA (iii) HYPOTHETICAL: No (iv) ANTI-SENSE: No (vi) ORIGINAL SOURCE: Synthetically prepared (vii) IMMEDIATE SOURCE: Same (x) PUBLICATION INFORMATION: US-A-5,147,777

(xi) SEQUENCE DESCRIPTION: SEQ ID NO:2:
ATAATCCACC TATCCCAGTA GGAGAAAT    28

(2) INFORMATION FOR SEQ ID NO:3:

(i) SEQUENCE CHARACTERISTICS:
(A) LENGTH: 40 nucleotides
(B) TYPE: Nucleic acid
(C) STRANDEDNESS: Single
(D) TOPOLOGY: Linear (ii) MOLECULE TYPE: HIV-I DNA primer (iii) HYPOTHETICAL: No (iv) ANTI-SENSE: No (vi) ORIGINAL SOURCE: Synthetically prepared (vii) IMMEDIATE SOURCE: Same (x) PUBLICATION INFORMATION: None (xi) SEQUENCE DESCRIPTION: SEQ ID NO:3:
CTAAAGGGTT CCTTTGGTCC TTGTCTTATG TCCAGAATGC    40

(2) INFORMATION FOR SEQ ID NO:4:

(i) SEQUENCE CHARACTERISTICS:
(A) LENGTH: 40 nucleotides
(B) TYPE: Nucleic acid
(C) STRANDEDNESS: Single
(D) TOPOLOGY: Linear (ii) MOLECULE TYPE: Primer for HIV-I DNA (iii) HYPOTHETICAL: No (iv) ANTI-SENSE: No (vi) ORIGINAL SOURCE: Synthetically prepared (vii) IMMEDIATE SOURCE: Same ( x ) PUBLICATION INFORMATION: None ( x i ) SEQUENCE DESCRIPTION: SEQ ID NO:4:

GATGGATGAC AAATAATCCA CCTATCCCAG TAGGAGAAAT    40

( 2 ) INFORMATION FOR SEQ ID NO:5:

( i ) SEQUENCE CHARACTERISTICS:
        ( A ) LENGTH: 20 nucleotides
        ( B ) TYPE: Nucleic acid
        ( C ) STRANDEDNESS: Single
        ( D ) TOPOLOGY: Linear ( i i ) MOLECULE TYPE: Primer for b-globin DNA ( i i i ) HYPOTHETICAL: No ( i v ) ANTI-SENSE: No ( v i ) ORIGINAL SOURCE: Synthetically prepared ( v i i ) IMMEDIATE SOURCE: Same ( x ) PUBLICATION INFORMATION: US-A-5,147,777

( x i ) SEQUENCE DESCRIPTION: SEQ ID NO:5:

CAACTTCATC CACGTTCACC    20

( 2 ) INFORMATION FOR SEQ ID NO:6:

( i ) SEQUENCE CHARACTERISTICS:
        ( A ) LENGTH: 20 nucleotides
        ( B ) TYPE: Nucleic acid
        ( C ) STRANDEDNESS: Single
        ( D ) TOPOLOGY: Linear ( i i ) MOLECULE TYPE: Primer for b-globin DNA ( i i i ) HYPOTHETICAL: No ( i v ) ANTI-SENSE: No ( v i ) ORIGINAL SOURCE: Synthetically prepared ( v i i ) IMMEDIATE SOURCE: Same ( x ) PUBLICATION INFORMATION: US-A-5,147,777

( x i ) SEQUENCE DESCRIPTION: SEQ ID NO:6:

ACACAACTGT GTTCACTAGC    20

( 2 ) INFORMATION FOR SEQ ID NO:7:

( i ) SEQUENCE CHARACTERISTICS:
        ( A ) LENGTH: 41 nucleotides
        ( B ) TYPE: Nucleic acid
        ( C ) STRANDEDNESS: Single
        ( D ) TOPOLOGY: Linear ( i i ) MOLECULE TYPE: HIV-I DNA probe ( i i i ) HYPOTHETICAL: No ( i v ) ANTI-SENSE: No ( v i ) ORIGINAL SOURCE: Synthetically prepared ( v i i ) IMMEDIATE SOURCE: Same ( x ) PUBLICATION INFORMATION: US-A-5,147,777

( x i ) SEQUENCE DESCRIPTION: SEQ ID NO:7:

```
            ATCCTGGAAT  TAAATAAAAT  AGTAAGAATG  TATAGCCCTA  C          4 1
```

( 2 ) INFORMATION FOR SEQ ID NO:8:

( i ) SEQUENCE CHARACTERISTICS:
        ( A ) LENGTH: 31 nucleotides
        ( B ) TYPE: Nucleic acid
        ( C ) STRANDEDNESS: Single
        ( D ) TOPOLOGY: Linear ( i i ) MOLECULE TYPE: Probe for b-globin DNA ( i i i ) HYPOTHETICAL: No ( i v ) ANTI-SENSE: No ( v i ) ORIGINAL SOURCE: Synthetically prepared ( v i i ) IMMEDIATE SOURCE: Same ( x ) PUBLICATION INFORMATION: US-A-5,147,777

( x i ) SEQUENCE DESCRIPTION: SEQ ID NO:8:

```
            CCTCAAACAG  ACACCATGGT  GCACCTGACT  C          3 1
```